April 28, 1942. R. A. HARRIS Plant Pat. 510
PECAN TREE
Filed April 18, 1941
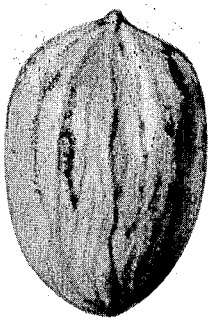
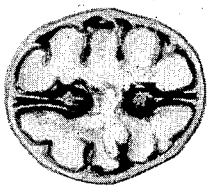
INVENTOR
Robert Alsey Harris
By Orville M. Kile
PLANT PATENT AGENT Patented Apr. 28, 1942

Plant Pat. 510

UNITED STATES PATENT OFFICE

510

PECAN TREE

Robert Alsey Harris, Riverside, Calif., assignor to Lawrence Sherwood, Fullerton, Calif.

Application April 18, 1941, Serial No. 389,239

1 Claim. (Cl. 47—62)

My new invention relates to improvements in the type of pecans known as the hickory pecan and particularly to the thin-shelled, general purpose varieties. It is a bud sport of the Altman variety, improved by reselection. The buds came from an Altman tree in Texas and were budded and developed by me on a plot on Chase Road in Riverside, which plot was my former home and adjoins my present residence.

This new variety has been asexually reproduced for a number of years and its characteristics have proved to be permanently fixed.

The outstanding points of difference between this new variety and its parent are the earlier maturity season, greater productivity and wider adaptability of the new variety. It matures early enough for the Thanksgiving market, which is an exceptional feature in pecans. And in all of my fifty years' specialization in growing pecans I have never seen a more productive variety when trees of a similar age are compared. It differs from its parent also in that it is more hardy and its nut is broader at the germ end, is thinner shelled, and has more even sutures in kernels which allows bitter membranes to drop out more freely.

The original illustration accompanying this application shows in black and white a perspective view and a cross-section view of specimens of this new variety, enlarged approximately one-third.

Following is a detailed description of the tree and fruit of this new variety of pecan.

*The tree*

Growth habit: Vigorous; very pendulous. Limbs unusually slim for the first two or three years.

Adaptability: Adaptive to a wide climatic zone and very hardy in a wide range of soil and moisture conditions. Unusually free from rosetting habit due no doubt to its superior structural qualities, particularly of bark and foliage, which enables the tree to draw necessary elements from the soil to combat this habit.

Productivity: Exceedingly productive and produces at an early age. Makes a good crop every year. Has in many situations produced fine crops under the same conditions in which other varieties failed to maintain good health or to produce crops.

Wood: New wood is very bright reddish brown, this being quite unusual in known commercial pecan varieties.

Foliage: Large and heavy.

Buds: Long and pointed. Same color as bark of current year's growth.

Blossoms: There is nothing unusual about the shape of the blossoms. Staminate bloom is full and very abundant and its maturity is properly timed to insure thorough fertilization of the pistallate bloom.

*The nuts*

Ripening: Nuts ripen evenly and almost all may be harvested at one time.

Quantity: Very abundant.

Maturity: Early, avoiding early winter and late fall frosts. In this locality (Riverside, California) it matures in time for the current crop to be marketed for the Thanksgiving season. Very few varieties mature this early and none which are similar to my new variety.

Tenacity: Nuts cling unusually well—better than any other variety known to me.

Cluster: Variety averages four nuts to a cluster, all of which mature and attain a large size.

Size: Approximately 1¾ inches long and one inch in diameter at its widest point, on an average, although many specimens run larger.

Weight: Averages 45 to 48 nuts to the pound.

Shape: Plump but slightly flattened. Base rounded; apex end broader than base end; point blunt, approximately mucronate.

Shell: Thin. Cracks and releases better than the usual pecan.

Color: Between Sayal Brown (Plate XXIX, Ridgway's) and Cinnamon-Brown (Plate XV), with shadings of reddish brown extending from the apex.

Kernel:

*Flavor.*—Exceptionally good, somewhat like a hickory-nut. Considered better-flavored than its parent.

*Shape.*—Plump.

*Texture.*—Fine-grained and firm.

*Sutures.*—Even, allowing bitter membranes to drop out freely.

*Comparison*

My new variety is more like Altman than any other known variety. However, the two varieties differ in many respects, some of which follow:

1. The tree of my variety is much more pendulous than Altman.

2. My variety is much more productive than Altman.

3. My variety matures its nuts earlier than Altman.

4. My variety has a much wider adaptability to varying conditions than Altman.

5. My variety is hardier than Altman.

6. My variety is more consistent in producing a good crop.

7. The nut of my variety is broader at the germ end than the nut of Altman.

8. The nut of my variety hulls better and releases its kernels better than Altman.

9. The nut of my variety has more even sutures in the kernels and thus allows the bitter membranes to drop out more freely.

10. The nut of my variety is thinner shelled than that of Altman.

11. Many who have tasted both varieties of nut think my new variety has a much superior flavor to that of Altman.

Having thus disclosed my invention, I claim:

The new and distinct variety of pecan tree herein described, characterized particularly by its vigorous and pendulous growth; its unusual hardiness; its wide adaptability to varying conditions of soil and moisture; its consistent production of large crops even under adverse circumstances in which other varieties fail to produce; its early maturing season; and its nuts that cling with a high degree of tenacity, ripen evenly, crack and release well, and have plump kernels of fine texture and excellent flavor.

ROBERT ALSEY HARRIS.